US00PP34339P2

(12) United States Plant Patent
Geibel

(10) Patent No.: US PP34,339 P2
(45) Date of Patent: Jun. 14, 2022

(54) ***PELARGONIUM* PLANT NAMED 'PACSAMARA'**

(50) Latin Name: ***Pelargonium* x *hortorum***
Varietal Denomination: Pacsamara

(71) Applicant: ELSNER pac JUNGPFLANZEN GbR, Thiendorf (DE)

(72) Inventor: Martin Geibel, Dresden (DE)

(73) Assignee: ELSNER pac JUNGPFLAZEN GbR, Thiendorf (NL)

( * ) Notice: Subject to any disclaimer, the term of this patent is extended or adjusted under 35 U.S.C. 154(b) by 0 days.

(21) Appl. No.: 17/474,948

(22) Filed: Sep. 14, 2021

(51) Int. Cl.
*A01H 5/02* (2018.01)
*A01H 6/42* (2018.01)

(52) U.S. Cl.
USPC ..... Plt./330

(58) Field of Classification Search
USPC ..... Plt./263.1, 324, 325, 330
See application file for complete search history.

*Primary Examiner* — Karen M Redden
(74) *Attorney, Agent, or Firm* — C. Anne Whealy

(57) ABSTRACT

A new and distinct Zonal Geranium plant named 'Pacsamara', characterized by its upright and uniformly rounded plant habit; moderate vigorous growth habit; freely basal branching habit; dark green-colored leaves; early and freely flowering habit; and red-colored semi-double flowers that are held above the foliar plane on strong peduncles.

1 Drawing Sheet

Botanical designation: *Pelargonium* x *hortorum*.
Cultivar denomination: 'PACSAMARA'.

BACKGROUND OF THE INVENTION

The present invention relates to a new and distinct cultivar of Zonal Geranium plant, botanically known as *Pelargonium* x *hortorum*, and hereinafter referred to by the cultivar name 'Pacsamara'.

The new Zonal Geranium plant is a product of a planned breeding program conducted by the Inventor in Dresden, Germany. The objective of the breeding program is to develop new uniform and early-flowering Zonal Geranium plants with dark green-colored leaves and numerous attractive flowers.

The new Zonal Geranium plant originated from a cross-pollination made by the Inventor of two unidentified proprietary selections of *Pelargonium* x *hortorum*, not patented, during the summer of 2016. Seed was collected from a number of potential parent plants, combined and sown. The new Zonal Geranium plant was discovered and selected by the Inventor as a single flowering plant from within the progeny of the stated mass cross-pollination in a controlled greenhouse environment in Dresden, Germany during the summer of 2017.

Asexual reproduction of the new Zonal Geranium plant by vegetative terminal cuttings in a controlled greenhouse environment in Dresden, Germany since January, 2018 has shown that the unique features of this new Zonal Geranium plant are stable and reproduced true to type in successive generations.

SUMMARY OF THE INVENTION

Plants of the new Zonal Geranium have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Pacsamara'. These characteristics in combination distinguish 'Pacsamara' as a new and distinct Zonal Geranium plant:

1. Upright and uniformly rounded plant habit.
2. Moderate vigorous growth habit.
3. Freely basal branching habit.
4. Dark green-colored leaves.
5. Early and freely flowering habit.
6. Red-colored semi-double flowers that are held above the foliar plane on strong peduncles.

Plants of the new Zonal Geranium can be compared to plants of the *Pelargonium* x *hortorum* 'Pacabel', disclosed in U.S. Plant Pat. No. 22,881. In side-by-side comparisons, plants of the new Zonal Geranium differ from plants of 'Pacabel' in the following characteristics:

1. Plants of the new Zonal Geranium are more freely branching than plants of 'Pacabel'.
2. Leaves of plants of the new Zonal Geranium are lighter green than leaves of plants of 'Pacabel'.
3. Peduncles of plants of the new Zonal Geranium are medium green in color whereas peduncles of plant of 'Pacabel' are greyish brown in color.

BRIEF DESCRIPTION OF THE PHOTOGRAPH

The accompanying colored photograph illustrates the overall appearance of the new Zonal Geranium plant showing the colors as true as it is reasonably possible to obtain in colored reproductions of this type. Colors in the photograph may differ slightly from the color values cited in the detailed botanical description which accurately describe the colors of the new Zonal Geranium plant. The photograph is a side perspective view of a typical flowering plant of 'Pacsamara' grown in a container.

DETAILED BOTANICAL DESCRIPTION

The aforementioned photograph and following observations, measurements and values describe plants grown in 19-cm containers during the spring, summer and autumn in a glass-covered greenhouse in Dresden, Germany and under cultural practices typical of commercial Zonal Geranium production. During the production of the plants, day temperatures averaged 18° C., night temperatures averaged 16° C. and light levels ranged from 15 klux to 100 klux. Plants were four months old when the photograph was taken and nine months old when the detailed description was taken. In the following detailed description, color references are made to The Royal Horticultural Society Colour Chart, 1995 Edition, except where general terms of ordinary dictionary significance are used.

Botanical classification: *Pelargonium* x *hortorum* 'Pacsamara'.

Parentage:

*Female, or seed, parent*.—Unidentified proprietary selection of *Pelargonium* x *hortorum*, not patented.

*Male or pollen parent*.—Unidentified proprietary selection of *Pelargonium* x *hortorum*, not patented.

Propagation:

*Type*.—By vegetative terminal cuttings.

*Time to initiate roots, summer*.—About 18 days at temperatures about 20° C.

*Time to initiate roots, winter*.—About 22 days at temperatures about 20° C.

*Time to produce a rooted young plant, summer*.—About four weeks at temperatures about 20° C.

*Time to produce a rooted young plant, winter*.—About four weeks at temperatures about 18° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant and growth habit*.—Upright and uniformly rounded plant habit; inverted triangle; densely foliated; moderately vigorous growth habit; moderate rapid growth rate; freely basal branching habit with about six primary lateral branches each with about two secondary lateral branches developing per plant; pinching is typically not required.

*Plant height, to top of foliar plane*.—About 26 cm.

*Plant height, to top of floral plane*.—About 36 cm.

*Plant width*.—About 40 cm.

*Lateral branches*.—Length: About 23 cm. Diameter: About 8 mm. Internode length: About 1 cm. Strength: Strong. Texture and luster: Densely pubescent; semi-glossy. Color, developing: Close to 144A. Color, developed: Close to 147B.

Leaf description:

*Arrangement*.—Opposite; simple.

*Length*.—About 5.4 cm.

*Width*.—About 8.3 cm.

*Shape*.—Rounded; roughly reniform.

*Apex*.—Rounded.

*Base*.—Cordate, open.

*Margin*.—Crenate with shallow and divergent indentations.

*Venation pattern*.—Palmate.

*Texture and luster, upper surface*.—Pubescent, rough; coriaceous; matte.

*Texture and luster, lower surface*.—Pubescent; coriaceous; glossy.

*Color*.—Developing and fully expanded leaves, upper surface: Close to 147A; venation, close to 147A; central zonal pattern, close to 200A. Developing and fully expanded leaves, lower surface: Close to 147B; venation, close to 146B.

*Petioles*.—Length: About 6 cm. Diameter: About 3 mm. Texture and luster, upper and lower surfaces: Pubescent; rough; matte. Color, upper and lower surfaces: Close to 146A.

Flower description:

*Flower arrangement and flowering habit*.—Semi-double flowers arranged in roughly hemispherical umbels arising from apical leaf axils; umbels displayed above the foliar plane on strong peduncles; flowers face mostly upright to outwardly depending on position in the umbel; freely flowering habit with about 15 open flowers per umbel and numerous umbels developing per plant during the flowering season.

*Fragrance*.—None detected.

*Flowering season*.—Early flowering habit; plants begin flowering about 80 days after planting; in the garden in Germany, flowering begins in April and continues until frost in the autumn.

*Flower longevity*.—Flowers last about six to ten days on the plant; umbels last about three to four weeks on the plant; flowers persistent.

*Umbel height*.—About 6 cm.

*Umbel diameter*.—About 12 cm.

*Flower diameter*.—About 4.7 cm by 4.7 cm.

*Flower depth* (*height*).—About 2 cm.

*Flower buds*.—Length: About 9 mm. Diameter: About 6 mm. Shape: Elliptic. Texture and luster: Pubescent; matte. Color: Close to 144A.

*Petals*.—Quantity per flower: About nine; petals imbricate. Length, upper petal: About 2.6 cm. Length, lower petal: About 2.5 cm. Width, upper petals: About 1.5 cm. Width, lower petals: About 1.9 cm. Shape: Obovate. Apex: Rounded. Base: Cuneate. Margin: Entire; slightly undulate. Texture and luster, upper and lower surfaces: Smooth, glabrous; semi-glossy. Color: When opening and fully opened, upper surface: Close to 45B; venation, close to 45A; color does not change with subsequent development. When opening and fully opened, lower surface: Close to 43A; venation, close to 45A; color does not change with subsequent development.

*Petaloids*.—Quantity per flower: If present, up to two. Length: About 5 mm to 20 mm. Width: About 2 mm to 8 mm. Shape: Irregular. Apex: Rounded. Base: Cuneate. Margin: Entire; slightly undulate. Texture and luster, upper and lower surfaces: Smooth, glabrous; semi-glossy. Color: When opening and fully opened, upper surface: Close to 45B; venation, close to 45A; color does not change with subsequent development. When opening and fully opened, lower surface: Close to 43A; venation, close to 45A; color does not change with subsequent development.

*Sepals*.—Calyx length: About 1 cm. Calyx diameter: About 1.8 cm. Quantity per flower: Five arranged in a single whorl; not fused. Length: About 1 cm. Width: About 2 mm to 4 mm. Shape: Lanceolate. Apex: Acute. Base: Truncate. Margin: Entire. Texture and luster, upper surface: Glabrous; glossy. Texture and luster, lower surface: Pubescent; glossy.

Color, when developing, upper and lower surfaces: Close to 146B; towards the base, close to 166A. Color, fully developed, upper and lower surfaces: Close to 146B; towards the base, close to 166A.

*Peduncles* (*umbel stems*).—Length: About 14 cm. Diameter: About 3 mm. Strength: Strong. Angle: Mostly upright to slightly outwardly. Texture and luster: Pubescent; glossy. Color: Close to 146A.

*Pedicels* (*individual flower stems*).—Length: About 3.4 cm. Diameter: About 1 mm. Strength: Moderately strong; flexible. Texture and luster: Pubescent; glossy. Color: Close to 166A.

*Reproductive organs*.—Androecium: Stamen quantity per flower: About nine. Filament length: About 7 mm. Filament color: Close to 57C; towards the base, close to 155D. Anther size: About 0.5 mm by 1 mm. Anther shape: Tubular. Anther color: Close to 59A. Pollen amount: Abundant. Pollen color: Close to 169C. Gynoecium: Pistil quantity per flower: One. Pistil length: About 9 mm. Stigma diameter: About 3 mm. Stigma shape: Five-parted. Stigma color: Close to 51A. Style length: About 3 mm. Style color: Close to 51A. Ovary color: Close to 177A. Seeds and fruits: To date, seed and fruit development have not been observed on plants of the new Zonal Geranium.

Pathogen & pest resistance: To date, plants of the new Zonal Geranium have not been observed to be resistant to pathogens and pests common to Zonal Geranium plants.

Temperature tolerance: Plants of the new Zonal Geranium have been observed to tolerate temperatures ranging from about 0.5° C. to about 40° C.

It is claimed:

1. A new and distinct Zonal Geranium plant named 'Pacsamara' as illustrated and described.

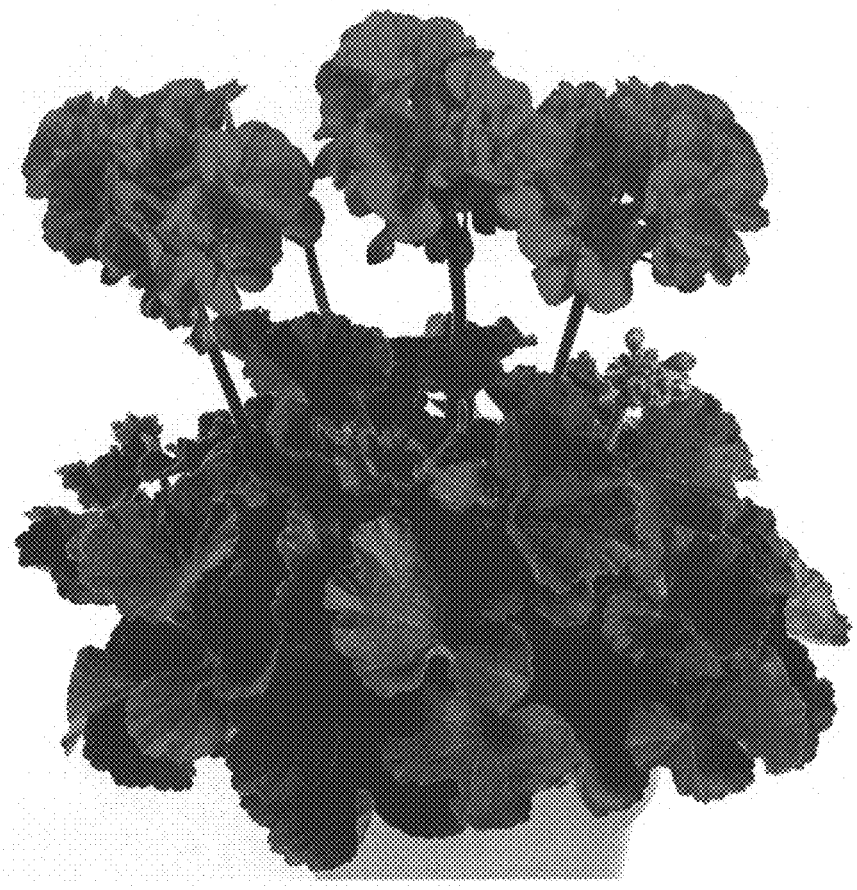

* * * * *